(12) United States Patent
Kim et al.

(10) Patent No.: US 9,207,191 B2
(45) Date of Patent: Dec. 8, 2015

(54) APPARATUS AND METHOD FOR CONTROLLING TEMPERATURE OF MATCHING MATERIAL

(71) Applicant: Electronics and Telecommunications Research Institute, Daejeon (KR)

(72) Inventors: Jang Yeol Kim, Daejeon (KR); Jong Moon Lee, Cheongju-si (KR); Hyuk Je Kim, Daejeon (KR); Seong Ho Son, Daejeon (KR); Soon Ik Jeon, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 14/561,336

(22) Filed: Dec. 5, 2014

(65) Prior Publication Data

US 2015/0168315 A1     Jun. 18, 2015

(30) Foreign Application Priority Data

Dec. 17, 2013   (KR) ........................ 10-2013-0157459

(51) Int. Cl.
*G01N 22/00*     (2006.01)
*A61B 6/00*      (2006.01)

(52) U.S. Cl.
CPC . *G01N 22/00* (2013.01); *A61B 6/44* (2013.01)

(58) Field of Classification Search
CPC .................................. G01N 22/00; A61B 6/44
See application file for complete search history.

(56) References Cited

U.S. PATENT DOCUMENTS

| | | | |
|---|---|---|---|
| 7,798,107 B2 | 9/2010 | Chian et al. | |
| 7,996,066 B2* | 8/2011 | Schlagheck et al. | 600/474 |
| 9,078,587 B2* | 7/2015 | Gulsen et al. | 1/1 |
| 2007/0224169 A1* | 9/2007 | Sliwa et al. | 424/93.2 |
| 2011/0149068 A1 | 6/2011 | Son et al. | |
| 2014/0342395 A1* | 11/2014 | Seibel et al. | 435/30 |

FOREIGN PATENT DOCUMENTS

| | | |
|---|---|---|
| JP | 2003042750 A | 2/2003 |
| KR | 1020110071819 A | 6/2011 |

* cited by examiner

*Primary Examiner* — Evan Pert
(74) *Attorney, Agent, or Firm* — William Park & Associates Ltd.

(57) ABSTRACT

An apparatus and method of controlling a temperature of a matching material used in an apparatus for generating a tomographic image is disclosed. The method includes measuring a temperature of a matching material in which an object is immersed in an apparatus for measuring a shape of an object, setting a set temperature at which an amplitude and a phase of an electromagnetic wave that passes through the matching material are maintained, based on the measured temperature of the matching material, and controlling the temperature of the matching material to be higher than the set temperature.

20 Claims, 8 Drawing Sheets

APPARATUS AND METHOD FOR CONTROLLING TEMPERATURE OF MATCHING MATERIAL

CROSS-REFERENCE TO RELATED APPLICATION

This application claims the priority benefit of Korean Patent Application No. 10-2013-0157459, filed on Dec. 17, 2013, in the Korean Intellectual Property Office, the disclosure of which is incorporated herein by reference.

BACKGROUND

1. Field of the Invention

Embodiments of the present invention relate to an apparatus and a method of controlling a temperature of a matching material, and more particularly, to an apparatus and a method of maintaining a property of a matching material associated with an electromagnetic wave loss by controlling a temperature of the matching material used in an apparatus for generating a tomographic image. "This invention was funded by the MISP (Ministry of Science, ICT & Future Planning), Korea in the ICT R&D Program 2013 into an information and communication technology (ICT) research development program in 2013"

2. Description of the Related Art

In recent times, research into microwave tomography (MT) using an electromagnetic wave is being conducted to develop a new technology for diagnosing breast cancer.

An apparatus for generating a tomographic image may immerse a breast in a predetermined matching material that allows an electromagnetic wave to readily penetrate the breast, and reconfigure a tomographic image of the breast based on wave scattering data that penetrates the breast.

The apparatus for generating the tomographic image may use amplitude and phase information of the electromagnetic wave that passes through the breast as key information to be used to reconfigure the tomographic image of the breast.

However, the matching material has a property of causing a loss in the electromagnetic wave that passes through the matching material, and the property may vary based on a temperature of the matching material.

When the property of the matching material is maintained, the amplitude and phase information of the electromagnetic wave that passes through the breast may be measured precisely based on the property of the matching material. However, when the property of the matching material changes, a time may needed to reconfigure the tomographic image or an error may occur in the reconfiguring.

Furthermore, the property of the matching material may vary in response to the temperature of the matching material decreasing based on a period of time elapsing because the temperature of the matching material is higher than a general room temperature.

Accordingly, there is a need for an apparatus and a method of preventing the amplitude and phase information of the electromagnetic wave that passes through the breast from being deteriorated due to the change in the property of the matching material based on a period of time elapsing.

SUMMARY

An aspect of the present invention provides an apparatus and a method of preventing amplitude and phase information of an electromagnetic wave received by an apparatus for generating a tomographic image from being deteriorated based on a period of time elapsing by controlling a temperature of a matching material used in the apparatus for generating the tomographic image.

According to an aspect of the present invention, there is provided a method of controlling a temperature of a matching material, the method including measuring a temperature of a matching material in which an object is immersed in an apparatus for measuring a shape of an object immersed in a matching material using an electromagnetic wave, setting a set temperature at which an amplitude and a phase of an electromagnetic wave that passes through the matching material are maintained, based on the measured temperature of the matching material, and controlling the temperature of the matching material to be higher than the set temperature.

The controlling may include increasing the temperature of the matching material using a heater when the temperature of the matching material is below the set temperature, and maintaining the temperature of the matching material by circulating the matching material using a pump when the temperature of the matching material is above the set temperature.

The increasing may include suspending an operation of the heater when a temperature of a matching material adjacent to the heater is above a predetermined block temperature.

The maintaining of the temperature of the matching material may include suspending the operation of the heater, and circulating, using the pump, the matching material of which the temperature is increased by the heater when the temperature of the matching material is above the set temperature.

The measuring may include measuring an upper temperature and a lower temperature of the matching material using a temperature sensor of which a length varies based on the water level of the matching material.

The controlling may include controlling the temperature of the matching material using at least one of proportional control, integral control, and differential control.

According to an aspect of the present invention, there is provided a method of generating a tomographic image, the method including outputting an electromagnetic wave towards an object immersed in a matching material, controlling a temperature of the matching material through which the electromagnetic wave passes, receiving the electromagnetic wave that passes through the matching material of which the temperature is controlled and the object, and generating a tomographic image of the object using the output electromagnetic wave and the received electromagnetic wave.

The controlling may include measuring the temperature of the matching material, setting a set temperature at which an amplitude and a phase of the electromagnetic wave that passes through the matching material are maintained, based on the measured temperature of the matching material, increasing the temperature of the matching material using a heater when the temperature of the matching material is below the set temperature, and maintaining the temperature of the matching material by circulating the matching material using a pump when the temperature of the matching material is above the set temperature.

According to an aspect of the present invention, there is provided an apparatus for controlling a temperature of a matching material, the apparatus including a temperature measurer to measure a temperature of a matching material in which an object is immersed in an apparatus for measuring a shape of an object immersed in a matching material using an electromagnetic wave, a set temperature setter to set a set temperature at which an amplitude and a phase of an electromagnetic wave that passes through the matching material are maintained, based on the measured temperature of the matching material, and a temperature controller to control the temperature of the matching material to be higher than the set temperature.

The temperature controller may include a matching material temperature increaser to increase the temperature of the matching material using a heater when the temperature of the matching material is below the set temperature, and a matching material temperature maintainer to maintain the temperature of the matching material by circulating the matching material using a pump when the temperature of the matching material is above the set temperature.

According to an aspect of the present invention, there is provided an apparatus for generating a tomographic image, the apparatus including a matching material temperature controller to control a temperature of a matching material through which an electromagnetic wave passes, an electromagnetic wave transception unit comprising a plurality of electromagnetic wave transceivers that outputs an electromagnetic wave towards an object immersed in a matching material and a plurality of electromagnetic wave transceivers that receives an electromagnetic wave that passes through a matching material of which a temperature is controlled and the object, and a tomographic image generator to generate a to tomographic image of an object using an output electromagnetic wave and a received electromagnetic wave.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
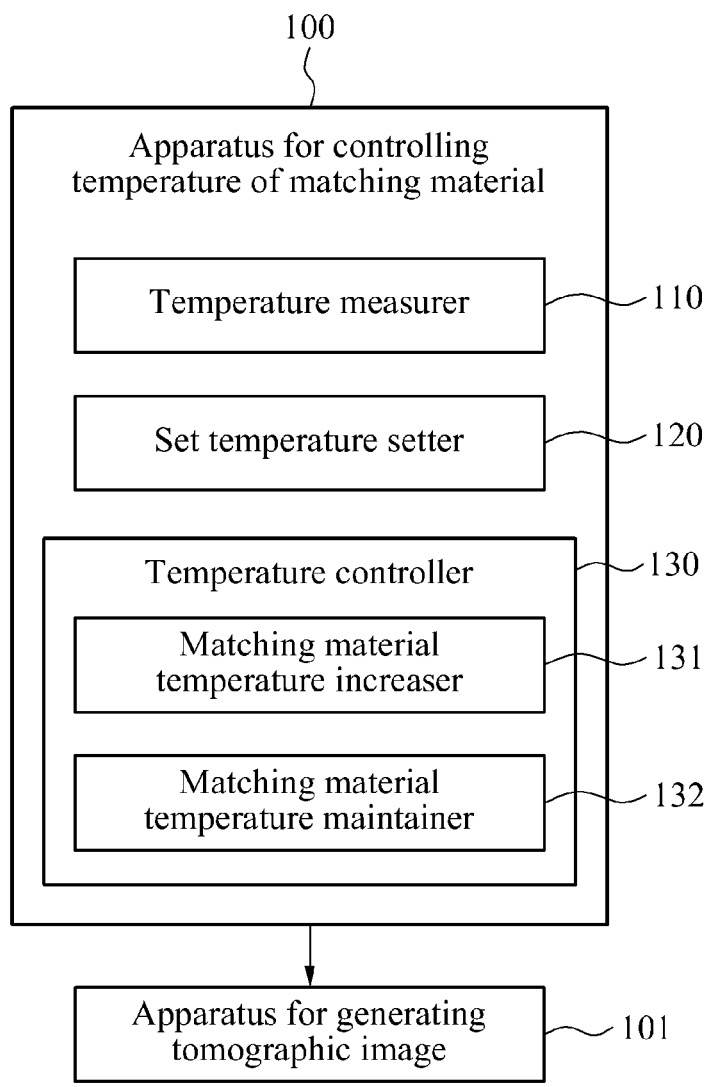
FIG. 1 is a block diagram illustrating an apparatus for controlling a temperature of a matching material according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures. According to an exemplary embodiment of the present invention, a method of controlling a temperature of a matching material is conducted by an apparatus for controlling a temperature of a matching material.

FIG. 1 is a block diagram illustrating an apparatus 100 for controlling a temperature of a matching material according to an embodiment of the present invention.

An apparatus 101 for generating a tomographic image generates a tomographic image of an object immersed in a matching material using an electromagnetic wave. For example, the term "object" may refer to a target object to be measured to generate the tomographic image, including such as an object to be immersed in a matching material or a portion of a user body, for example, breasts. The term "matching material" may refer to a liquid that enables the electromagnetic wave to readily penetrate an interior of an object, for example, a breast.

For example, the apparatus 101 for generating the tomographic image outputs an electromagnetic wave to an object immersed in a matching material in a plurality of directions sequentially, receives an electromagnetic wave that passes through the object, and generates a tomographic image of the object based on a difference between the received electromagnetic wave and the output electromagnetic wave.

Here, an electromagnetic wave loss may occur in the electromagnetic wave that passes through the object in a frequency domain based on a property of the matching material. For example, the property of the matching material associated with the electromagnetic wave loss may include at least one of a dielectric constant, a conductivity, a specific heat, and a molecular weight of the matching material.

The property of the matching material associated with the electromagnetic wave loss may be susceptible to a change in a temperature of the matching material.

Accordingly, when the temperature of the matching material changes while the apparatus 101 for generating the tomographic image sequentially outputs the electromagnetic wave to the object, the property of the matching material may change, resulting in an increase in the electromagnetic wave loss of the electromagnetic wave that passes through the object. When the electromagnetic wave loss of the electromagnetic wave that passes through the object increases, the difference between the received electromagnetic wave and the output electromagnetic wave occurs due to another factor aside from the object through which the electromagnetic wave passes. Consequently, an error may occur in the tomographic image of the object, or generating the tomographic image of the object may be difficult.

In this example, the apparatus 100 for controlling the temperature of the matching material may prevent, by maintaining the temperature of the matching material in which the object is immersed, the error in the tomographic image caused by a temperature decrease in the matching material while the apparatus 101 for generating the tomographic image generates the tomographic image by outputting the electromagnetic wave to the object immersed in the matching material in a plurality of directions sequentially.

Referring to FIG. 1, the apparatus 100 for controlling the temperature of the matching material includes a temperature measurer 110, a set temperature setter 120, and a temperature controller 130.

The temperature measurer 110 measures a temperature of a matching material in which an object is immersed in the apparatus 101 for generating the tomographic image.

The temperature measurer 110 measures a temperature of an upper portion of the matching material and a temperature of a lower portion of the matching material using a temperature sensor. For example, the temperature measurer 110 measures the temperature of the upper portion of the matching material adjacent to an electromagnetic wave transception unit of the apparatus 101 for generating the tomographic image and the temperature of the lower portion of the matching material adjacent to a heater of the temperature controller 130. The electromagnetic wave transception unit includes a plurality of transceivers that outputs an electromagnetic wave or receives an electromagnetic wave output from another electromagnetic wave transception unit.

The temperature sensor used by the temperature measurer 110 may refer to a temperature sensor of which a length varies based on a water level of a matching material.

The set temperature setter 120 sets a set temperature at which an amplitude and a phase of an electromagnetic wave that passes through a matching material are maintained, based on the temperature of the matching material measured by the temperature measurer 110.

The temperature controller 130 controls the temperature of the matching material to be higher than the set temperature using a matching material temperature increaser 131 and a matching material temperature maintainer 132.

In this example, the temperature controller 130 controls the temperature of the matching material using a least one of proportional control, integral control, and differential control. For example, the temperature controller 130 controls the temperature of the matching material using proportional-integral-derivative (PID) control that combines all of the proportional control, the integral control, and the differential control.

In one example, when the temperature of the matching material is below the set temperature, the temperature controller 130 operates the matching material temperature increaser 131.

In this example, the matching material temperature increaser 131 increases the temperature of the matching material using a heater. The heater used by the matching material temperature increaser 131 may be a heater of which a size varies based on a water level of the matching material.

When a temperature of the matching material adjacent to the heater is above a predetermined block temperature, the matching material temperature increaser 131 prevents a problem, such as an over current or a short circuit by suspending an operation of the heater. Here, the matching material temperature increaser 131 suspends the heating by the heater by blocking a power supplied to the heater.

In another example, when the temperature of the matching material is above the set temperature, the temperature controller 130 operates the matching material temperature maintainer 132. In this example, the matching material temperature maintainer 132 maintains the temperature of the matching material by circulating the matching material using a pump.

When the temperature of the matching material is above the set temperature set by the set temperature setter 120, the matching material temperature maintainer 132 suspends the operation of the heater operated by the matching material temperature increaser 131, and circulates, using the pump, the matching material of which the temperature is increased by the heater.

In this example, a lower portion of the matching material of which a temperature is increased by the heater is mixed with an upper portion of the matching material of which a temperature is decreased by a contact with air and an object in response to the circulation of the matching material. Further, the temperature of the upper portion of the matching material is increased by the lower portion of the matching material, resulting in a decrease in a speed at which the temperature is decreased by the contact with the air and the object. Accordingly, when the matching material is circulated using the pump, the temperature of the matching material may be maintained for a relatively long period of time because the temperature of the upper portion of the matching material decreases slower when the matching material is circulated than when the matching material is not circulated.

The heater overheated by the heating may be cooled down because the temperature of the lower portion of the matching material is decreased by the upper portion of the matching material.

Accordingly, the apparatus 100 for controlling the temperature of the matching material controls the temperature of the matching material to be maintained above the set temperature by increasing the temperature of the matching material to be higher than the set temperature when the temperature of the matching material decreases below the set temperature, and maintaining the temperature of the matching material by circulating the matching material when the temperature is above the set temperature.

Figure 2:
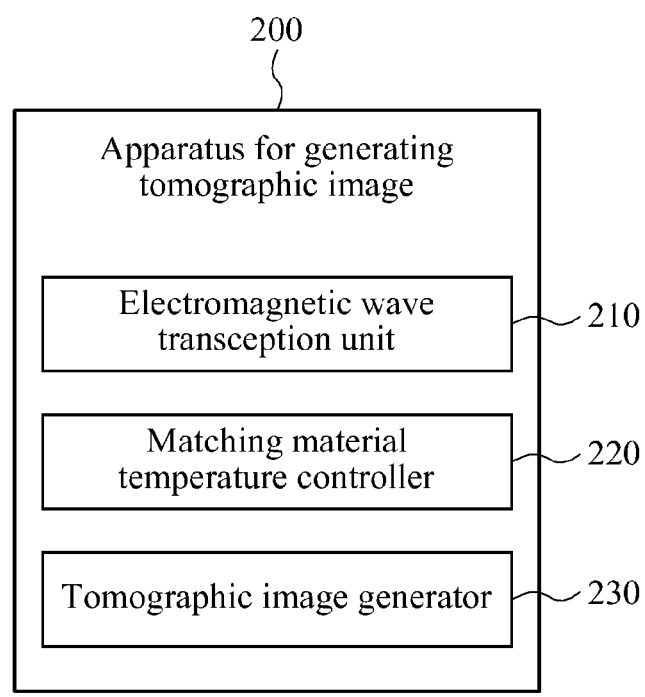
FIG. 2 is a block diagram illustrating an apparatus for generating a tomographic image according to an embodiment of the present invention.

FIG. 2 is a block diagram illustrating an apparatus 200 for generating a tomographic image according to an embodiment of the present invention.

FIG. 2 is an example of the apparatus 200 for generating the tomographic image that controls a temperature of a matching material.

Referring to FIG. 2, the apparatus 200 for generating the tomographic image includes an electromagnetic wave transception unit 210, a matching material temperature controller 220, and a tomographic image generator 230.

The electromagnetic wave transception unit 210 outputs an electromagnetic wave towards an object immersed in a matching material. For example, the electromagnetic wave transception unit 210 outputs the electromagnetic wave to the object immersed in the matching material in a plurality of directions sequentially using a plurality of electromagnetic wave transceivers.

The electromagnetic wave transception unit 210 receives an electromagnetic wave that passes through a matching material of which a temperature is controlled by the matching material temperature controller 220 and an object. For example, when the plurality of electromagnetic wave transceivers of the electromagnetic wave transception unit 210 does not output an electromagnetic wave, the plurality of electromagnetic wave transceivers of the electromagnetic wave transception unit 210 may receive an electromagnetic wave output from one of other electromagnetic wave transceivers.

The matching material temperature controller 220 controls the temperature of the matching material through which the electromagnetic wave output from the electromagnetic wave transception unit 210 passes.

In this example, the matching material temperature controller 220 measures the temperature of the matching material, and based on the measured temperature of the matching material, sets a set temperature at which an amplitude and a phase of the electromagnetic wave that passes through the matching material are maintained. The matching material temperature controller 220 controls the temperature of the matching material to be higher than the set temperature.

In one example, when the temperature of the matching material is below a predetermined set temperature, the matching material temperature controller 220 may increase the temperature of the matching material using a heater. In another example, when the temperature of the matching material is above the predetermined set temperature, the matching material temperature controller 220 may maintain the temperature of the matching material by circulating the matching material using a pump.

The matching material temperature controller 220 includes a temperature measurer, a set temperature setter, and a temperature controller as the apparatus 100 for controlling the temperature of the matching material of FIG. 1. Descriptions of the temperature measurer 110, the set temperature setter 120, and the temperature controller 130 previously provided in FIG. 1 may be applied to operations of the temperature measurer, the set temperature setter, and the temperature controller included in the matching material temperature controller 220 of FIG. 2, and thus, repeated descriptions will be omitted here for conciseness.

The tomographic image generator 230 generates a tomographic image of the object using the electromagnetic wave output from the electromagnetic wave transception unit 210 and the electromagnetic wave received by the electromagnetic wave transception unit 210.

Figure 3:
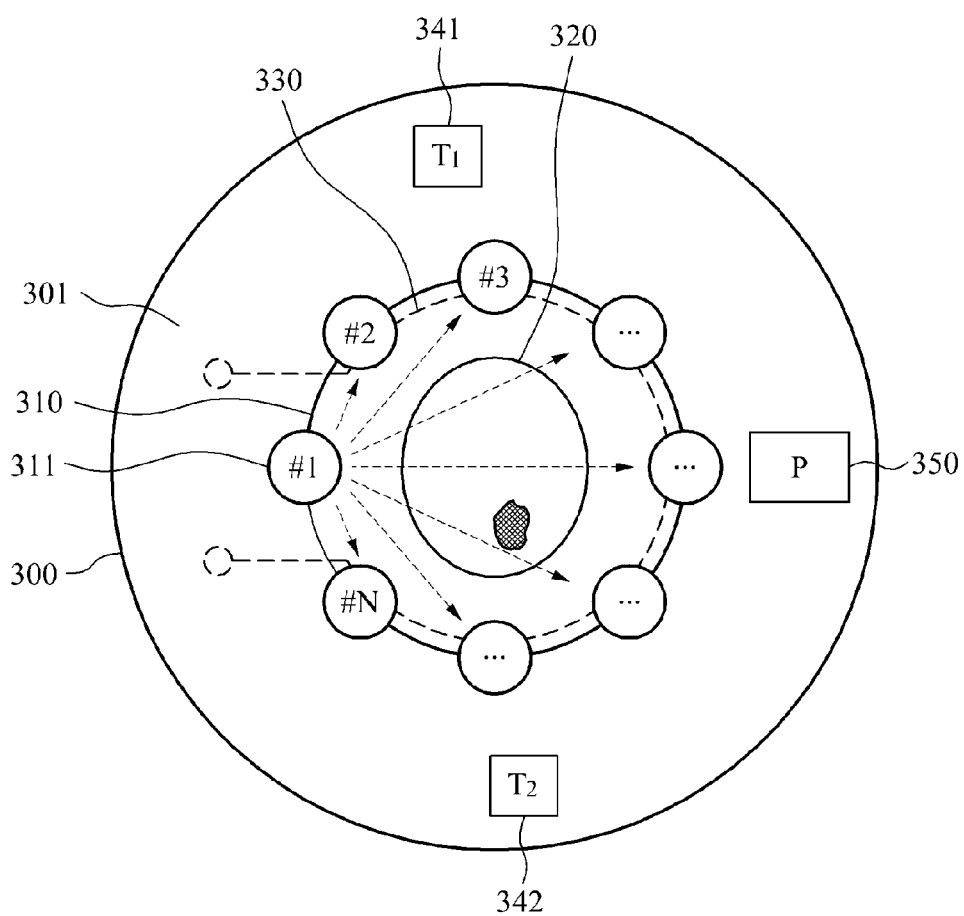
FIG. 3 is a top view of an apparatus for generating a tomographic image according to an embodiment of the present invention.

FIG. 3 is a top view of an apparatus for generating a tomographic image according to an embodiment of the present invention.

The apparatus 200 for generating the tomographic image includes a water tank 300 containing a matching material 301. The electromagnetic wave transception unit 210 of the apparatus 200 for generating the tomographic image includes a plurality of electromagnetic wave transceivers 311 and a structure 310 to fix a position of a plurality of electromagnetic wave transceivers. Here, the structure 310 and the plurality of electromagnetic wave transceivers 311 are immersed in the matching material 301. The plurality of electromagnetic wave transceivers 311 is disposed in the structure 310 in a form of a circle surrounding an object 320 as shown in FIG. 3.

When a first electromagnetic wave transceiver (#1) outputs an electromagnetic wave, a second electromagnetic wave transceiver (#2) through an N-th electromagnetic wave transceiver (#N) receive the electromagnetic wave output from the first electromagnetic wave transceiver (#1). In this example, the electromagnetic wave received by the second electromagnetic wave transceiver (#2) and the N-th electromagnetic wave transceiver (#N) may be identical to the electromagnetic wave that is reduced due to an electromagnetic wave loss in the matching material while the electromagnetic wave output from the first electromagnetic wave transreceiver (#1) passes through the matching material based on the electromagnetic wave loss in the matching material because the electromagnetic wave received by the second electromagnetic wave transceiver (#2) and the N-th electromagnetic wave transceiver (#N) does not pass through the object 320. Accordingly, the tomographic image generator 230 may not use an electromagnetic wave identical to the electromagnetic wave output from the first electromagnetic wave transceiver (#1) in generating the tomographic image from among the electromagnetic waves received by the second electromagnetic wave transceiver (#2) through the N-th electromagnetic wave transceiver (#N).

When the first electromagnetic wave transceiver (#1) suspends outputting of an electromagnetic wave, the second electromagnetic wave transceiver (#2) may output an electromagnetic wave, and the first electromagnetic wave transceiver (#1), and a third electromagnetic wave transceiver (#3) through the N-th electromagnetic wave transceiver (#N) may receive the electromagnetic wave output from the second electromagnetic wave transceiver (#2).

In detail, the electromagnetic wave transception unit 210 may iterate the aforementioned process by changing an electromagnetic wave transceiver that outputs an electromagnetic wave until the the N-th electromagnetic wave transceiver (#N) outputs an electromagnetic wave.

The N-th electromagnetic wave transceiver (#N) may output an electromagnetic wave subsequent to a predetermined period of time elapsing from a point in time at which the first electromagnetic wave transceiver (#1) outputs an electromagnetic wave because the first electromagnetic wave transceiver (#1) through the N-th electromagnetic wave transceiver (#N) sequentially output an electromagnetic wave. However, a temperature of a matching material making contact with air and the object 320 may decrease based on a period of time elapsing. When the temperature of the matching material decreases, a property associated with an electromagnetic wave loss such as a dielectric constant, a conductivity, a specific heat, and a molecular weight of the matching material may change. As a result, a deviation may appear between an electromagnetic wave that does not pass through the object 320 from among electromagnetic waves output from the first electromagnetic wave transceiver (#1) and an electromagnetic wave that does not pass through the object 320 from among electromagnetic waves output from the N-th electromagnetic wave transceiver (#N).

Accordingly, the matching material temperature controller 220 may maintain a temperature of the matching material 301 above a set temperature using a heater 330, a first temperature sensor 341, a second temperature sensor 342, and a pump 350.

The heater 330 may refer to a heater in a ring type corresponding to a size and a form of the structure 310 as shown in FIG. 3. The heater 330 may be disposed at a lower portion of the structure 310, and increase a temperature of the matching material 301 adjacent to the to plurality of electromagnetic wave transceivers 311.

The plurality of electromagnetic wave transceivers 311 is provided in the form of the circle surrounding the object 320 as shown in FIG. 3. Accordingly, although a temperature of the matching material adjacent to the third electromagnetic wave transceiver (#3) is above the set temperature, a temperature of the matching material adjacent to the N-th electromagnetic wave transceiver (#N) disposed distant from the third electromagnetic wave transceiver (#3) may be below the set temperature. Thus, the matching material temperature controller 220 may measure both the temperature of the matching material adjacent to the third electromagnetic wave transceiver (#3) and the temperature of the matching material adjacent to the N-th electromagnetic wave transceiver (#N) by disposing the first temperature sensor 341 and the second temperature sensor 342 in an opposite direction centering the structure 310 as shown in FIG. 3.

The matching material temperature controller 220 disposes the two temperature sensors with reference to FIG. 3, however, a greater number of temperature sensors may be provided. For example, at least one temperature sensor may be provided adjacent to each of the plurality of electromagnetic wave transceivers 311.

The matching material temperature controller 220 may maintain the temperature of the matching material adjacent to the plurality of electromagnetic wave transceivers 311 through the matching material being circulated by mixing a lower portion of the matching material of which a temperature is increased by the heater 300 and an upper portion of the matching material of which a temperature is decreased by a contact with air and an object.

Figure 4:
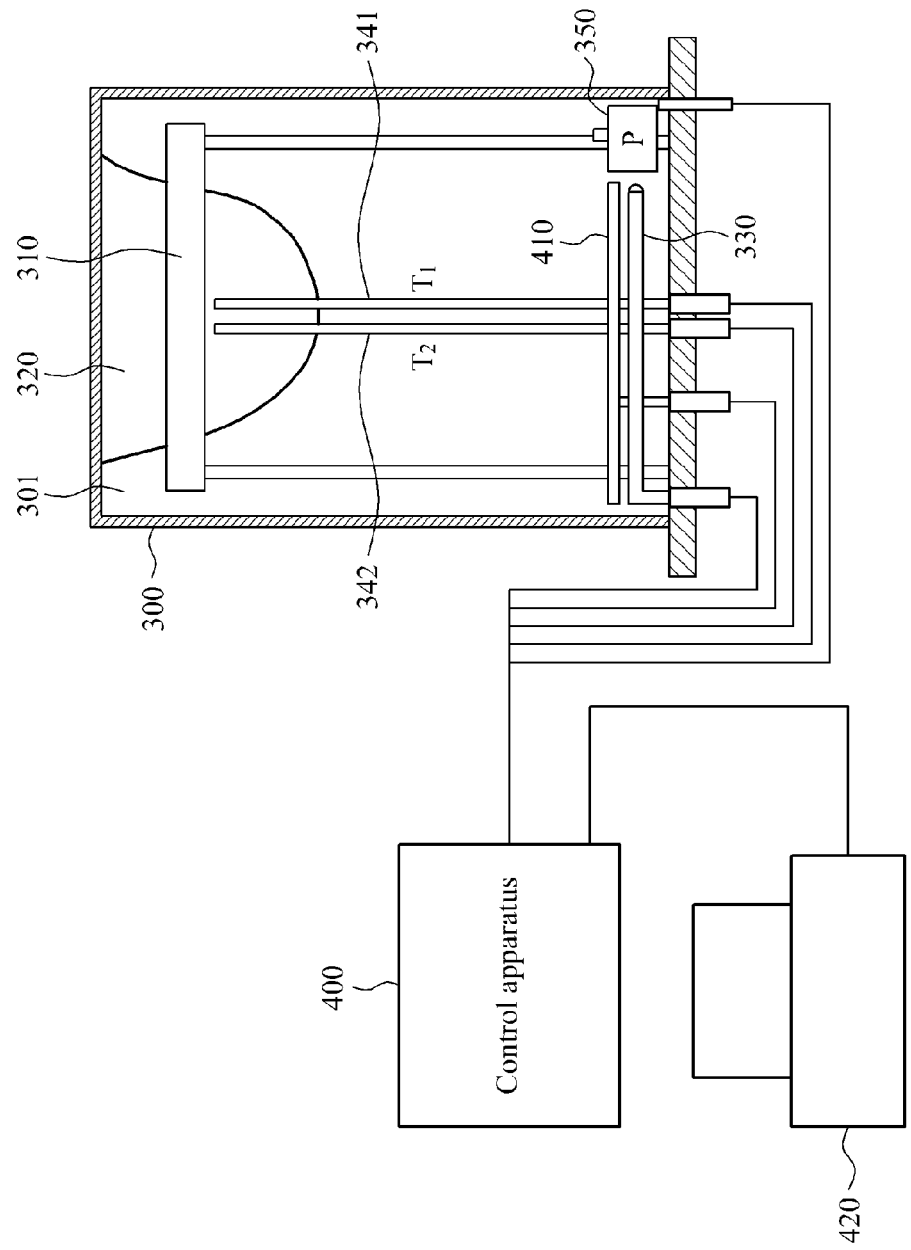
FIG. 4 is a side cross-sectional view of an apparatus for generating a tomographic image according to an embodiment of the present invention.

FIG. 4 is a side cross-sectional view of an apparatus for generating a tomographic image according to an embodiment of the present invention.

The structure 310 in which the plurality of electromagnetic wave transceivers 311 is provided is disposed based on a height of the object 320 immersed in the matching material 301 as shown in FIG. 4.

The first temperature sensor 341 and the second temperature sensor 342 are disposed facing each other at a height similar to the plurality of electromagnetic wave transceivers 311, and measure a temperature of an upper portion of the matching material 301 adjacent to the plurality of electromagnetic wave transceivers 311. Here, the height of the first temperature sensor 341 and the second temperature sensor 342 may vary based on a water level of the matching material 301.

The first temperature sensor 341 and the second temperature sensor 342 may measure a temperature of a lower portion of the matching material 301 adjacent to the heater 330. Here, a third temperature sensor adjacent to the heater 330 may be added in order to measure the temperature of the lower portion of the matching material 301.

In this example, the temperature of the upper portion of the matching material 301 and the temperature of the lower portion of the matching material 301 measured by the first temperature sensor 341 and the second temperature sensor 342 may be transmitted to a control apparatus 400.

The control apparatus 400 may be the apparatus 100 for controlling the temperature of the matching material of FIG. 1, or include the matching material temperature controller 220 of FIG. 2. The control apparatus 400 controls heating performed by the heater 330 or circulating of the matching material 301 performed by the pump 350 based on the transmitted temperature of the upper portion of the matching material 301 and the temperature of the lower portion of the matching material 301.

The control apparatus 400 determines that the heater 330 is overheated by a factor such as an over current or a short circuit when the temperature of the lower portion of the matching material 301 is excessively high, and prevents damage to the heater 330 by suspending the heating by the heater 330.

In this example, a protection cap 410 is provided above the heater 330 in order to protect the heater 330 from an external contact and prevent a burn.

The control apparatus 400 communicates with an external personal computer (PC) 420 including a recommended standard-232 (RS-232) communication module. The control apparatus 400 transmits, to the external PC 420, the temperature of the upper portion of the matching material 301 and the temperature of the lower portion of the matching material 301. The control apparatus 400 controls the temperature of the matching material 301 by controlling operations of the heater 330 and the pump 350 based on a control instruction received from the external PC 420. For example, the control apparatus 400 enables a user to control the temperature of the matching material 301 remotely by providing a communication function with the external PC 420.

Figure 5:
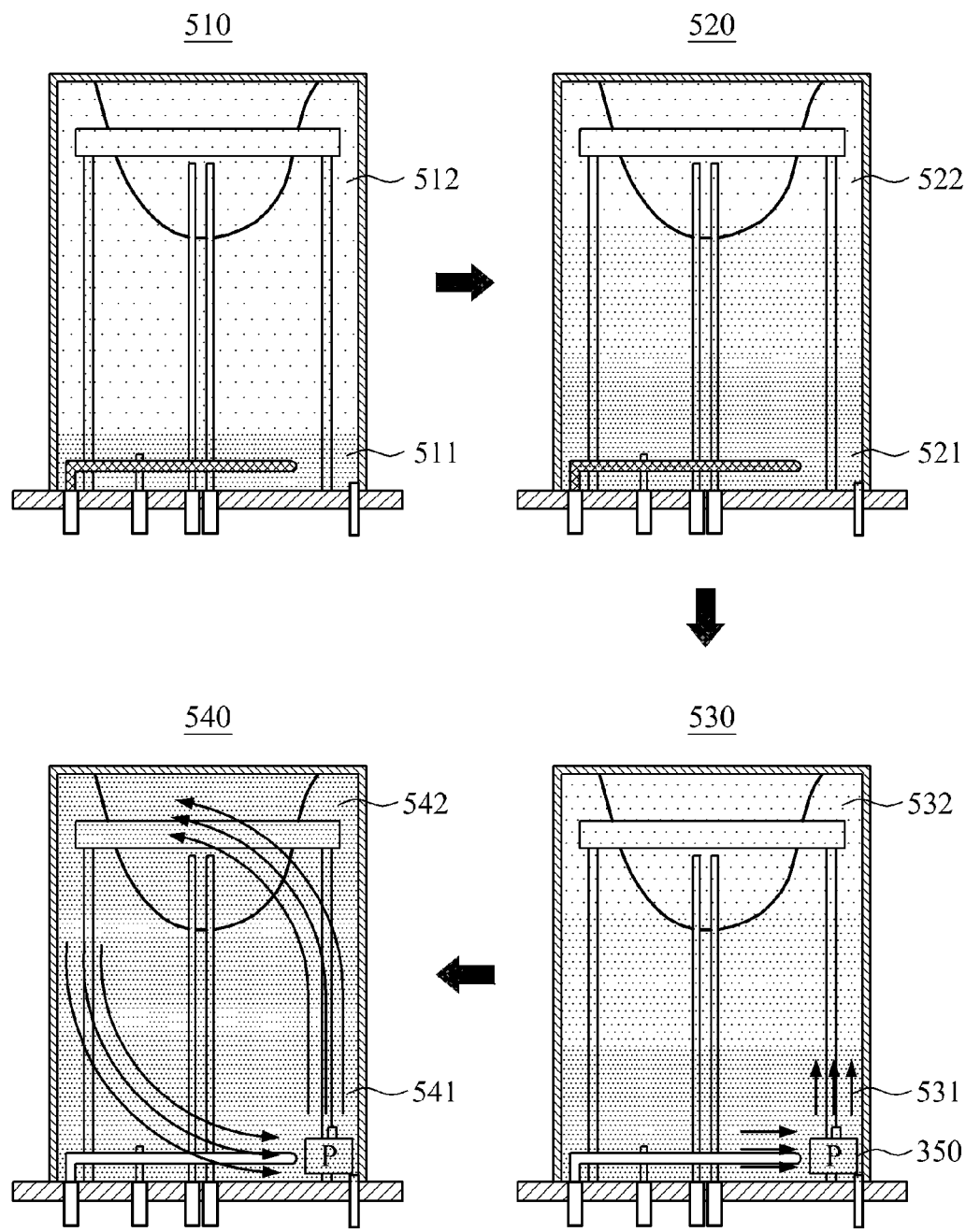
FIG. 5 is a diagram illustrating an example of a process of controlling a temperature of a matching material according to an embodiment of the present invention.

FIG. 5 is a diagram illustrating an example of a process of controlling a temperature of a matching material according to an embodiment of the present invention.

FIG. 5 is an example of a process in which the temperature measurer 110 measures a temperature of an upper portion of a matching material, and based on a result of the measurement, the temperature controller 130 controls a temperature of the matching material in a state in which the set temperature setter 120 sets a set temperature.

In operation 510, the temperature controller 130 increases a temperature of a matching material by operating a heater. In this example, a temperature of a lower portion 511 of the matching material adjacent to the heater increases directly to a set temperature, however, a temperature of an upper portion 512 of the matching material in which electromagnetic wave transceivers and an object are provided is yet to increase to the set temperature.

In operation 520, the temperature controller 130 maintains the heater operated in operation 510. In this example, the temperature of the matching material increases to the set temperature up to a middle height of the matching material while the upper portion 522 is below the set temperature as shown in FIG. 5. In addition, although the temperature of the upper portion 522 is below the set temperature, the temperature of the lower portion 521 adjacent to the heater is above the set temperature. Here, the temperature controller 130 suspends the heating by the heater during a predetermined period of time, and prevents the heater and the matching material from being overheated. When the temperature of the upper portion 522 of the matching material is above the set temperature, the temperature controller 130 performs operation 530.

In operation 530, the temperature controller 130 suspends the heating by the heater, and prevents the temperature of the matching material from rising excessively. The temperature controller 130 vertically circulates the matching material by operating the pump 350.

In operation 540, the temperature controller 130 verifies whether a temperature of an upper portion 542 of the matching material decreases below the set temperature. In this example, when a lower portion 541 of the matching material with a relatively high temperature is mixed with the upper portion 542 of the matching material with a relatively low temperature, the temperature of the matching material is a median value between the temperature of the lower portion 541 and the temperature of the upper portion 542, and the temperature of the upper portion 542 gradually decreases as shown in FIG. 5.

When the temperature of the upper portion 542 of the matching material decreases to the set temperature, the temperature controller 130 operates the heater and performs operation 520 to maintain the set temperature of the matching material.

Figure 6:
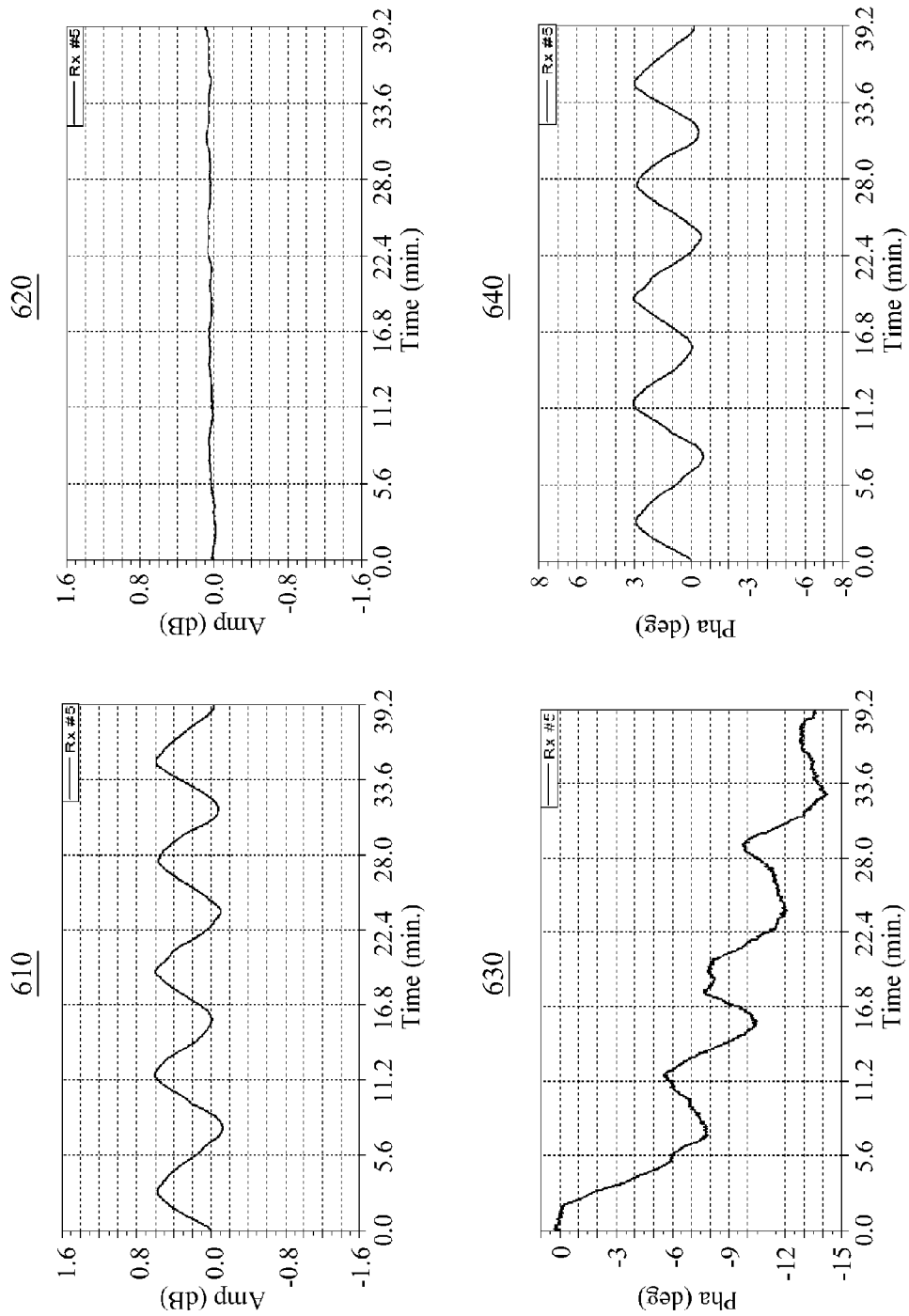
FIG. 6 illustrates graphs of examples of amplitude and phase information of an electromagnetic wave received by an apparatus for generating a tomographic image according to an embodiment of the present invention.

FIG. 6 illustrates graphs of examples of amplitude and phase information of an electromagnetic wave received by an apparatus for generating a tomographic image according to an embodiment of the present invention.

A graph 610 illustrates an amplitude of an electromagnetic wave received by electromagnetic wave transceivers based on a period of time elapsing in a state in which a temperature of a matching material is not controlled. A graph 630 illustrates a phase of an electromagnetic wave received by electromagnetic wave transceivers based on a period of time elapsing in a state in which a temperature of a matching material is not controlled.

A graph 620 illustrates an amplitude of an electromagnetic wave received by electromagnetic wave transceivers based on a period of time elapsing in a state in which a temperature of a matching material is controlled by the apparatus 100 for controlling the temperature of the matching material or the matching material temperature controller 220. A graph 640 illustrates a phase of an electromagnetic wave received by electromagnetic wave transceivers based on a period of time elapsing in a state in which a temperature of a matching material is controlled.

When the temperature of the matching material is not controlled, the temperature of the matching material decreases based on a period of time elapsing. When the temperature of the matching material decreases based on the period of time elapsing, the amplitude of the electromagnetic wave received by the electromagnetic wave transceivers is reduced as shown in the graph 610. Also, the phase of the electromagnetic wave received by the electromagnetic wave transceivers is reduced as shown in the graph 630.

When the apparatus 100 for controlling the temperature of the matching material or the matching material temperature controller 220 according to an embodiment of the present invention controls the temperature of the matching material, the temperature of the matching material is maintained despite the period of time elapsing. When the temperature of the matching material is maintained, a property of the matching material associated with an electromagnetic wave loss may not change.

Accordingly, the amplitude of the electromagnetic wave received by the electromagnetic wave transceivers is maintained irrespective of the period of time elapsing as shown in the graph 620. The phase of the electromagnetic wave received by the electromagnetic wave transceivers is maintained by changing at predetermined intervals irrespective of the period of time elapsing as shown in the graph 640.

The apparatus 100 for controlling the temperature of the matching material or the matching material temperature controller 220 according to an embodiment of the present invention prevents a change and an error in the electromagnetic wave loss based on a period of time elapsing by controlling the temperature of the matching material. When the change and the error in the electromagnetic wave loss are prevented, the apparatus for generating the tomographic image may generate a tomographic image more rapidly or precisely.

Figure 7:
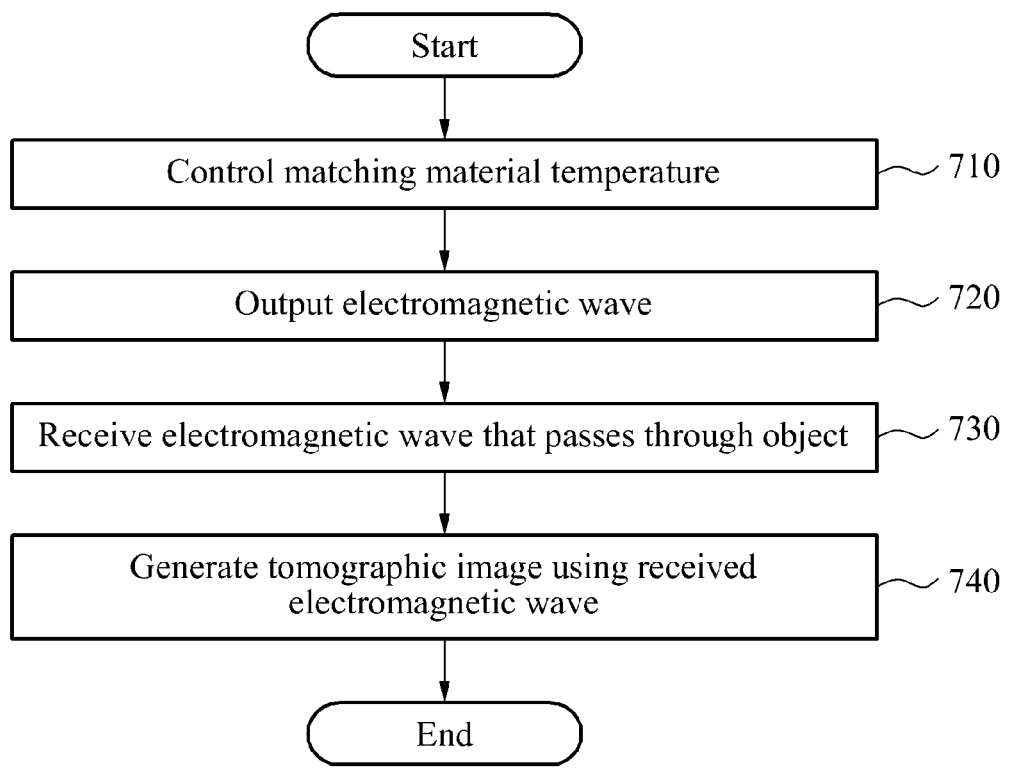
FIG. 7 is a flowchart illustrating a method of generating a tomographic image according to an embodiment of the present invention.

FIG. 7 is a flowchart illustrating a method of generating a tomographic image according to an embodiment of the present invention.

In operation 710, the matching material temperature controller 220 of the apparatus 200 for generating the tomographic image controls a temperature of a matching material through which an electromagnetic wave passes.

In this example, the matching material temperature controller 220 measures the temperature of the matching material, and based on the measured temperature of the matching material, sets a set temperature at which an amplitude and a phase of the electromagnetic wave that passes through the matching material are maintained. The matching material temperature controller 220 controls the temperature of the matching material to be higher than the set temperature.

A process of controlling the temperature of the matching material will be discussed in greater detail with reference to FIG. 8.

In operation 720, the electromagnetic wave transception unit 210 outputs an electromagnetic wave towards an object immersed in the matching material of which the temperature is controlled in operation 710. For example, the electromagnetic wave transception unit 210 outputs the electromagnetic wave to the object immersed in the matching material using a plurality of electromagnetic wave transceivers in a plurality of directions sequentially. Here, the plurality of electromagnetic wave transceivers is included in the electromagnetic wave transception unit 210.

In operation 730, the electromagnetic wave transception unit 210 receives the electromagnetic wave output in operation 720. In this example, electromagnetic wave transceivers remaining subsequent to excluding the electromagnetic wave transceiver that outputs the electromagnetic wave in operation 720 from among the plurality of electromagnetic wave transceivers receive the electromagnetic wave output in operation 720.

The electromagnetic wave received by the remaining electromagnetic wave transceivers may be the electromagnetic wave that passes through the matching material of which the temperature is controlled in operation 710 and the object.

In operation 740, the tomographic image generator 230 generates a tomographic image of the object using the electromagnetic wave output in operation 720 and the electromagnetic wave received in operation 730.

For example, the tomographic image generator 230 compares the electromagnetic wave output in operation 720 and the electromagnetic wave received in operation 730 to identify a difference between the electromagnetic wave output in operation 720 and the electromagnetic wave received in operation 730, and generates the tomographic image of the object using the identified difference.

Figure 8:
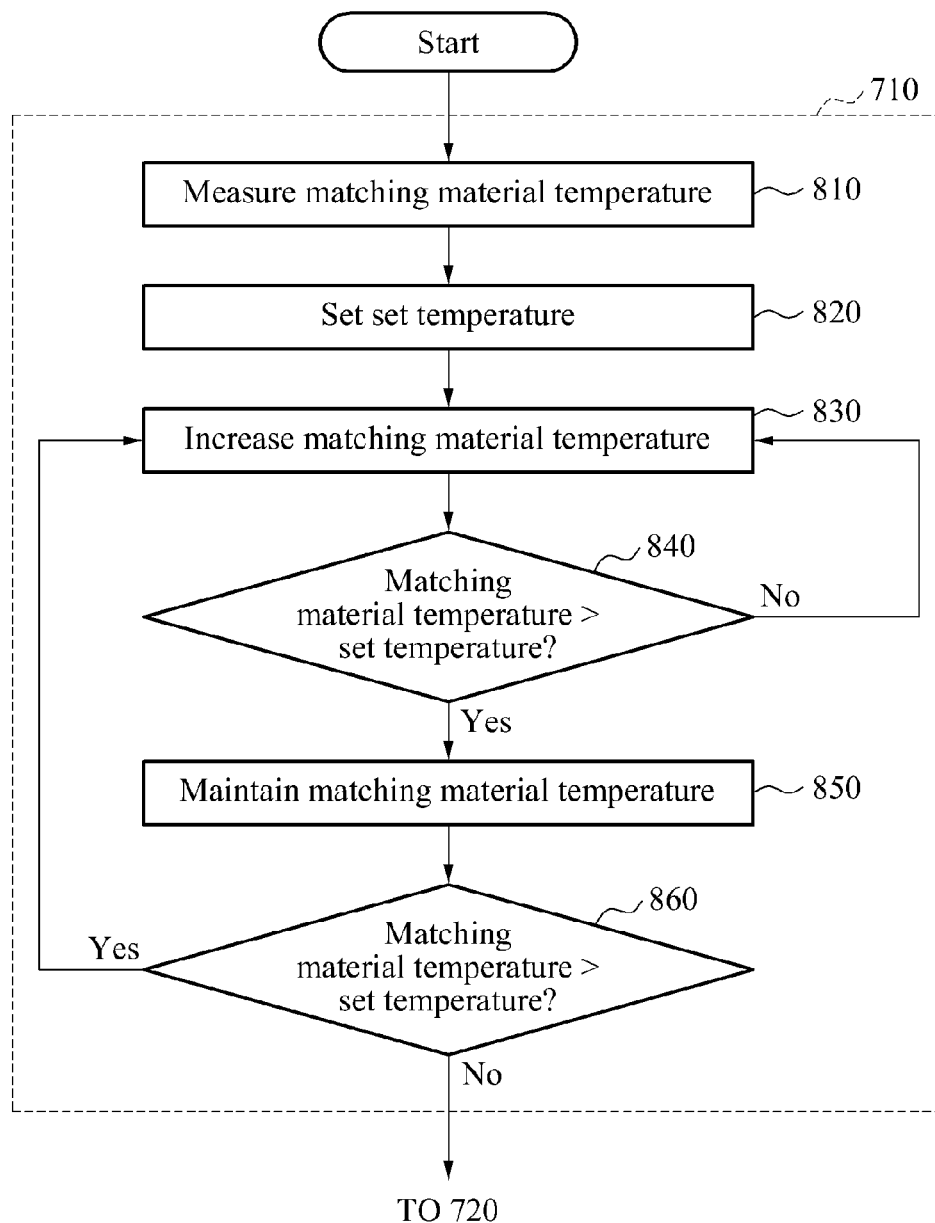
FIG. 8 is a flowchart illustrating a method of controlling a temperature of a matching material according to an embodiment of the present invention.

FIG. 8 is a flowchart illustrating a method of controlling a temperature of a matching material according to an embodiment of the present invention. Operation 810 through operation 860 of FIG. 8 may be included in operation 710 of FIG. 7.

Operation 810 through operation 860 of FIG. 8 may be performed in the apparatus 100 for controlling the temperature of the matching material separate from the apparatus 101 for generating the tomographic image.

In operation 810, the temperature measurer 110 measures a temperature of a matching material in which an object is immersed in the apparatus 101 for generating the tomographic image.

The temperature measurer 110 measures a temperature of an upper portion of the matching material and a temperature of a lower portion of the matching material using a temperature sensor. For example, the temperature measurer 110 measures the temperature of the upper portion of the matching material adjacent to the electromagnetic wave transception unit of the apparatus 101 for generating the tomographic image and the temperature of the lower portion of the matching material adjacent to the heater of the temperature controller 130.

The temperature measurer 110 displays the measured temperature on a control apparatus or an external PC in real time. Here, the temperature measurer 110 displays the measured temperature in a unit of "0.1" degree.

In operation 820, the set temperature setter 120 sets a set temperature at which an amplitude and a phase of an electromagnetic wave that passes through a matching material are maintained, based on the temperature of the matching material measured in operation 810.

In this example, when the temperature of the lower portion of the matching material is excessively high in operation 810, the set temperature setter 120 sets to block an operation of the heater. The set temperature setter 120 compares the temperature of the lower portion of the matching material and the upper portion of the matching material, and measures a temperature deviation between the upper portion and the lower portion of the matching material.

The set temperature setter 120 sets a control method of the temperature controller 130. For example, the set temperature setter 120 sets a PID control method as the control method of the temperature controller 130, thus allowing the temperature controller 130 to control a temperature absent an overshoot, hunting, or delay in responding.

In operation 830, the temperature controller 130 increases the temperature of the matching material using the heater. In this example, the temperature controller 130 suspends an operation of a pump.

In operation 840, the temperature controller 130 verifies whether the temperature increased in operation 830 is above the set temperature set in operation 820.

When the temperature increased in operation 830 is below the set temperature set in operation 820, the temperature controller 130 iteratively performs operation 830 to allow the temperature of the matching material to be above the set temperature set in operation 820.

When the temperature increased in operation 830 is above the set temperature set in operation 820, the temperature controller 130 performs operation 850.

In operation 850, the temperature controller 130 maintains the temperature of the matching material by circulating the matching material using the pump. In this example, the temperature controller 130 suspends the operation of the heater operated in operation 830, and circulates, using the pump, the matching material of which the temperature is increased by the heater.

In operation 860, the temperature controller 130 verifies whether the temperature of the matching material circulated in operation 850 is above the set temperature set in operation 820.

When the temperature circulated in operation 850 is below the set temperature set in operation 820, the temperature controller 130 performs operation 830 to allow the temperature of the matching material to be above the set temperature set in operation 820.

When the temperature circulated in operation 850 is above the set temperature set in operation 820, the temperature controller 130 iteratively performs operation 850, or allows the electromagnetic wave transception unit 210 to perform 720.

Accordingly, the temperature controller 130 maintains the temperature of the matching material to be higher than the set temperature by iteratively performing operation 830 through operation 850 while the apparatus 101 for generating the tomographic image generates the tomographic image.

According to the present exemplary embodiment, it is possible to prevent amplitude and phase information of an electromagnetic wave received by an apparatus for generating a tomographic image from being deteriorated based on a period of time elapsing by controlling a temperature of a matching material used in the apparatus for generating the tomographic image.

According to the present exemplary embodiment, it is possible to readily and rapidly generate a tomographic image using an electromagnetic wave by preventing amplitude and phase information of an electromagnetic wave received by an apparatus for generating a tomographic image from being deteriorated based on a period of time elapsing.

The above-described exemplary embodiments of the present invention may be recorded in computer-readable media including program instructions to implement various operations embodied by a computer. The media may also include, alone or in combination with the program instructions, data files, data structures, and the like. Examples of computer-readable media include magnetic media such as hard disks, floppy disks, and magnetic tape; optical media such as CD ROM discs and DVDs; magneto-optical media such as floptical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described exemplary embodiments of the present invention, or vice versa.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A method of controlling a temperature of a matching material, the method comprising:

measuring a temperature of a matching material in which an object is immersed in an apparatus for measuring a shape of an object immersed in a matching material using an electromagnetic wave;

setting a set temperature at which an amplitude and a phase of an electromagnetic wave that passes through the matching material are maintained, based on the measured temperature of the matching material; and to controlling the temperature of the matching material to be higher than the set temperature.

2. The method of claim 1, wherein the controlling comprises:

increasing the temperature of the matching material using a heater when the temperature of the matching material is below the set temperature; and maintaining the temperature of the matching material by circulating the matching material using a pump when the temperature of the matching material is above the set temperature.

3. The method of claim 2, wherein a size of the heater varies based on a water level of the matching material.

4. The method of claim 2, wherein the increasing comprises:

suspending an operation of the heater when a temperature of a matching material adjacent to the heater is above a predetermined block temperature.

5. The method of claim 2, wherein the maintaining of the temperature of the matching material comprises:

suspending the operation of the heater, and circulating, using the pump, the matching material of which the temperature is increased by the heater when the temperature of the matching material is above the set temperature.

6. The method of claim 1, wherein the measuring comprises:

measuring a temperature of a matching material adjacent to an electromagnetic wave transceiver that outputs or receives an electromagnetic wave, and the temperature of the matching material adjacent to the heater.

7. The method of claim 1, wherein the measuring comprises:

measuring an upper temperature and a lower temperature of the matching material using a temperature sensor of which a length varies based on the water level of the matching material.

8. The method of claim 1, wherein the controlling comprises:

controlling the temperature of the matching material using at least one of proportional control, integral control, and differential control.

9. A method of generating a tomographic image, the method comprising:

outputting an electromagnetic wave towards an object immersed in a matching material;

controlling a temperature of the matching material through which the electromagnetic wave passes;

receiving the electromagnetic wave that passes through the matching material of which the temperature is controlled and the object; and generating a tomographic image of the object using the output electromagnetic wave and the received electromagnetic wave.

10. The method of claim 9, wherein the controlling comprises:

measuring the temperature of the matching material;

setting a set temperature at which an amplitude and a phase of the electromagnetic wave that passes through the matching material are maintained, based on the measured temperature of the matching material;

increasing the temperature of the matching material using a heater when the temperature of the matching material is below the set temperature; and maintaining the temperature of the matching material by circulating the matching material using a pump when the temperature of the matching material is above the set temperature.

11. An apparatus for controlling a temperature of a matching material, the apparatus comprising:

a temperature measurer to measure a temperature of a matching material in which an object is immersed in an apparatus for measuring a shape of an object immersed in a matching material using an electromagnetic wave;

a set temperature setter to set a set temperature at which an amplitude and a phase of an electromagnetic wave that passes through the matching material are maintained, based on the measured temperature of the matching material; and a temperature controller to control the temperature of the matching material to be higher than the set temperature.

12. The apparatus of claim 11, wherein the temperature controller comprises:

a matching material temperature increaser to increase the temperature of the matching material using a heater when the temperature of the matching material is below the set temperature; and a matching material temperature maintainer to maintain the temperature of the matching material by circulating the matching material using a pump when the temperature of the matching material is above the set temperature.

13. The apparatus of claim 12, wherein a size of the heater varies based on a water level of the matching material.

14. The apparatus of claim 12, wherein the matching material temperature increaser suspends an operation of the heater when a temperature of a matching material adjacent to the heater is above a predetermined block temperature.

15. The apparatus of claim 12, wherein the matching material temperature maintainer suspends the operation of the heater and maintains the temperature of the matching material by circulating the matching material of which the temperature is increased by the heater when the temperature of the matching material is above the set temperature.

16. The apparatus of claim 11, wherein the temperature measurer measures a temperature of a matching material adjacent to a transceiver that outputs or receives an electromagnetic wave, and the temperature of the matching material adjacent to the heater.

17. The apparatus of claim 11, wherein the temperature measurer measures an upper temperature of the matching material and a lower temperature of the matching material using a temperature sensor of which a length varies based on the water level of the matching material.

18. An apparatus for generating a tomographic image, the apparatus comprising:

a matching material temperature controller to control a temperature of a matching material through which an electromagnetic wave passes;

an electromagnetic wave transception unit comprising a plurality of electromagnetic wave transceivers that outputs an electromagnetic wave towards an object immersed in a matching material and a plurality of electromagnetic wave transceivers that receives an electromagnetic wave that passes through a matching material of which a temperature is controlled and the object; and a tomographic image generator to generate a tomographic image of an object using an output electromagnetic wave and a received electromagnetic wave.

19. The apparatus of claim 18, wherein the matching material temperature controller comprises:

a temperature measurer to measure the temperature of the matching material;

a set temperature setter to set a set temperature at which an amplitude and a phase of the electromagnetic wave that passes through the matching material are maintained, based on the temperature of the matching material; and a temperature controller to control the temperature of the matching material to be higher than the set temperature.

20. The apparatus of claim 19, wherein the temperature controller measures a temperature of a matching material adjacent to the plurality of electromagnetic wave transceivers that outputs an electromagnetic wave and the plurality of electromagnetic wave transceivers that receives an electromagnetic wave, and a temperature of the matching material adjacent to the heater.

* * * * *